United States Patent
Adachi

(10) Patent No.: US 7,032,132 B2
(45) Date of Patent: Apr. 18, 2006

(54) REPRODUCTION TEST SERVICE APPARATUS FOR MEDICAL SYSTEMS, MAINTENANCE SUPPORT INFORMATION MANAGEMENT APPARATUS, X-RAY CT SYSTEM, AND MAINTENANCE SERVICE CENTER APPARATUS

(75) Inventor: Akira Adachi, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 111 days.

(21) Appl. No.: 10/162,585

(22) Filed: Jun. 6, 2002

(65) Prior Publication Data

US 2003/0156683 A1    Aug. 21, 2003

(30) Foreign Application Priority Data

Feb. 15, 2002    (JP) .............................. 2002-039080

(51) Int. Cl.
*G06F 11/00*    (2006.01)
(52) U.S. Cl. ..................... 714/28; 714/17; 714/20; 714/25; 378/1
(58) Field of Classification Search .................. 714/20, 714/25, 28, 17; 707/202; 378/1
See application file for complete search history.

(56) References Cited

U.S. PATENT DOCUMENTS

| | | | |
|---|---|---|---|
| 4,991,193 A * | 2/1991 | Cecil et al. ................. 378/117 |
| 5,890,154 A * | 3/1999 | Hsiao et al. ................... 707/8 |
| 5,892,897 A * | 4/1999 | Carlson et al. ................ 714/37 |
| 6,067,639 A * | 5/2000 | Rodrigues et al. ............ 714/38 |
| 6,145,099 A * | 11/2000 | Shindou ....................... 714/37 |
| 6,202,199 B1 * | 3/2001 | Wygodny et al. ............ 717/125 |
| 6,212,256 B1 | 4/2001 | Miesbauer et al. |
| 6,587,969 B1 * | 7/2003 | Weinberg et al. ............. 714/46 |

FOREIGN PATENT DOCUMENTS

| | | |
|---|---|---|
| JP | 6-62130 | 3/1994 |
| JP | 11-338889 | 12/1999 |
| JP | 2001-67417 | 3/2001 |
| JP | 2001-202265 | 7/2001 |

OTHER PUBLICATIONS

Microsoft Computer Dictionary, Microsoft Press, 1999, 4th ed., pp 85.*

* cited by examiner

*Primary Examiner*—Robert Beausoliel
*Assistant Examiner*—Emerson Puente
(74) *Attorney, Agent, or Firm*—Oblon, Spivak, McClelland, Maier & Neustadt, P.C.

(57) ABSTRACT

In order to reproduce the past operations of a medical system, a reproduction test service apparatus stores a plurality of past log files directly or indirectly supplied from the medical system in a log file storage unit and reproduces the past operations of the medical system on a pseudo X-ray CT system in accordance with the stored log files.

11 Claims, 7 Drawing Sheets

REPRODUCTION TEST SERVICE APPARATUS FOR MEDICAL SYSTEMS, MAINTENANCE SUPPORT INFORMATION MANAGEMENT APPARATUS, X-RAY CT SYSTEM, AND MAINTENANCE SERVICE CENTER APPARATUS

CROSS-REFERENCE TO RELATED APPLICATIONS

This application is based upon and claims the benefit of priority from the prior Japanese Patent Application No. 2002-039080, filed Feb. 15, 2002, the entire contents of which are incorporated herein by reference.

BACKGROUND OF THE INVENTION

1. Field of the Invention

The present invention relates to a reproduction test service apparatus for medical systems, a maintenance support information management apparatus, an X-ray CT system, and a maintenance service center apparatus.

2. Description of the Related Art

Recently, the range of applicability of medical systems, for example, an X-ray CT system (X-ray computerized tomography apparatus) has been expanding. This is due to improvements in hardware performance (such as improvements in the sensitivity and resolution of sensors), development of diverse imaging techniques (such as the real preparation scan(real-prep.scan) automatically imaging timing by monitoring a density of contrast mediums, helical scan, and CT fluoroscopy), and improvements in software performance (such as improvements in image reconstruction processing and image processing).

For this reason, in the event of a fault, it will delay CT examination work, producing considerably adverse effects on the operation of the system. It is therefore required to ensure rapid recovery.

In the event of a fault, whether or not it can be corrected mostly depends on whether or not the cause can be identified accurately. If the cause is identified accurately, a correction manual will help eliminate the fault.

However, it is one of the most difficult jobs to identify the cause of a fault accurately.

BRIEF SUMMARY OF THE INVENTION

The object of the present invention is to identify the cause of a fault in a medical system in a short time and allow the system downtime to be reduced.

According to a first aspect of the present invention there is provided a reproduction test service apparatus that reproduces past operations of a medical system, comprising: a unit configured to receive a plurality of past log files directly or indirectly from the medical system; a unit configured to store the plurality of log files; a pseudo medical system; and a control unit configured to control the pseudo medical system based on the log files so as to allow a plurality of past operations of the medical system to be reproduced on the pseudo medical system.

According to a second aspect of the present invention there is provided a maintenance support information management apparatus connected to a plurality of medical systems and at least one maintenance service apparatus through electronic communications circuits, comprising: a unit configured to receive a plurality of log files representing a record of operations from each of the medical systems; a unit configured to store the log files; a unit configured to analyze the stored log files and determine the frequency of use of each operation; and a unit configured to provide the frequency of use of each operation or information obtained therefrom as requested by the maintenance service apparatus.

According to a third aspect of the present invention there is provided an X-ray CT system comprising: a gantry unit configured to collect data from a subject under examination; a reconstruction unit configured to reconstruct image data based on the collected data; a unit configured to store data collected at the occurrence of a fault and reconstruction conditions at the time of the fault; and a control unit configured to allow the reconstruction unit to reproduce the same operation as at the time of the fault under the same reconstruction conditions as the stored reconstruction conditions using the stored data at the occurrence of the fault.

According to a fourth aspect of the present invention there is provided an X-ray CT system comprising: a gantry unit configured to collect data from a subject under examination; a reconstruction unit configured to reconstruct image data based on the collected data; and a control unit configured to, in the event of a fault, diagnose the gantry unit and the reconstruction unit in order to determine the seriousness of the fault and restrict the operation of the gantry unit or the reconstruction unit based on the seriousness of the fault.

According to a fifth aspect of the present invention there is provided an X-ray CT system comprising: a gantry unit configured to collect data from a subject under examination; a preprocessing unit configured to preprocess the collected data; a reconstruction unit configured to reconstruct image data based on the preprocessed data; a data transfer unit configured to transfer data between the gantry unit and the preprocessing unit and between the preprocessing unit and the reconstruction unit; a diagnostic unit configured to make a diagnosis of whether each of the data transfer unit, the preprocessing unit and the reconstruction unit is operating properly; and a unit configured to store diagnostic data similar to the data collected by the gantry unit and used for diagnosis by the diagnostic unit.

According to a sixth embodiment of the present invention there is provided a maintenance service center apparatus connected to a plurality of medical systems by electronic communications circuits, comprising: a unit configured to receive log files containing fault conditions from the medical systems; a unit configured to analyze the log files to determine the seriousness of faults and determine restrictions on the operation of the medical systems based on the seriousness of faults; and a unit configured to transfer the restrictions on the operation to the medical systems.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

The system of the present invention is associated with various medical systems including ultrasonic diagnosis apparatuses, X-ray CT apparatuses (X-ray computerized tomography apparatuses), magnetic resonance imaging apparatuses (MRIs), and gamma camera apparatuses. In the description which follows, the invention will be described in terms of an X-ray CT system. The principles of the invention are also applicable to other medical systems.

Figure 1:
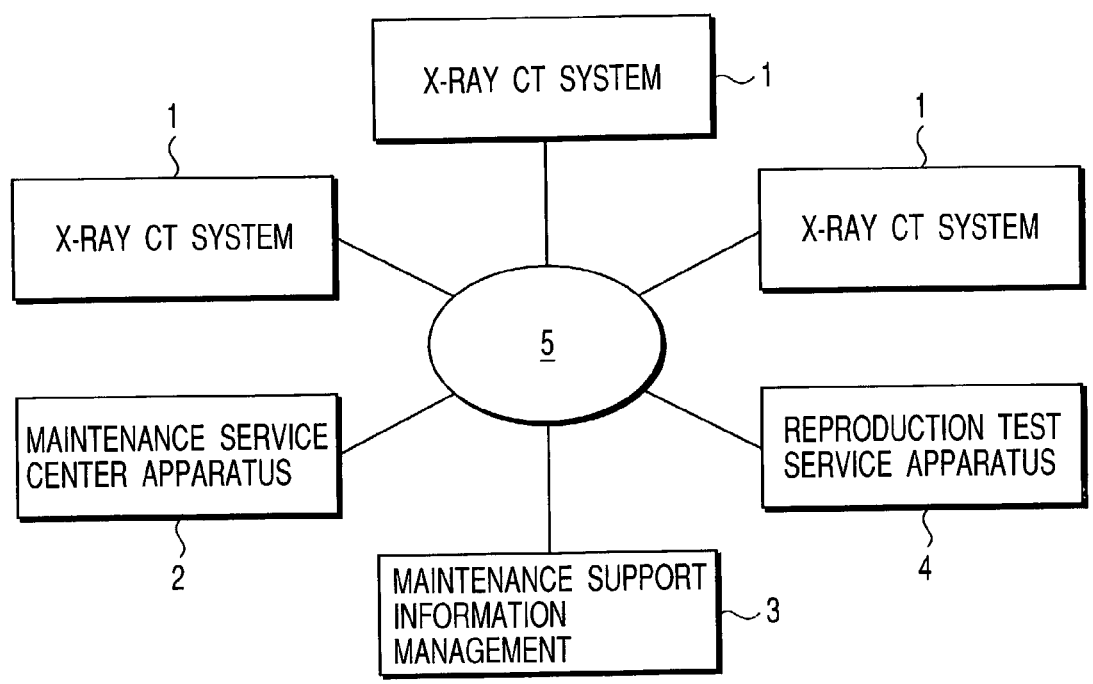
FIG. 1 is a schematic representation of a maintenance support system according to an embodiment of the present invention.

FIG. 1 shows the total configuration of the maintenance support system embodying the present invention. Two or more X-ray CT systems (X-ray computerized tomography apparatuses) 1 are connected to a maintenance service center apparatus 2, a maintenance support information management apparatus 3, and a reproduction test service apparatus 4 by electronic communications circuits 5 such as public or dedicated circuits. Each of the X-ray CT systems 1 is installed in a respective one of two or more hospital sites. The maintenance service center apparatus 2 is installed in a maintenance service center site. The maintenance support information management apparatus 3 is installed in a maintenance service center site, a maintenance support site, or a system maker technical site. The reproduction test service apparatus 4 is placed in the system maker technical site.

Figure 2:
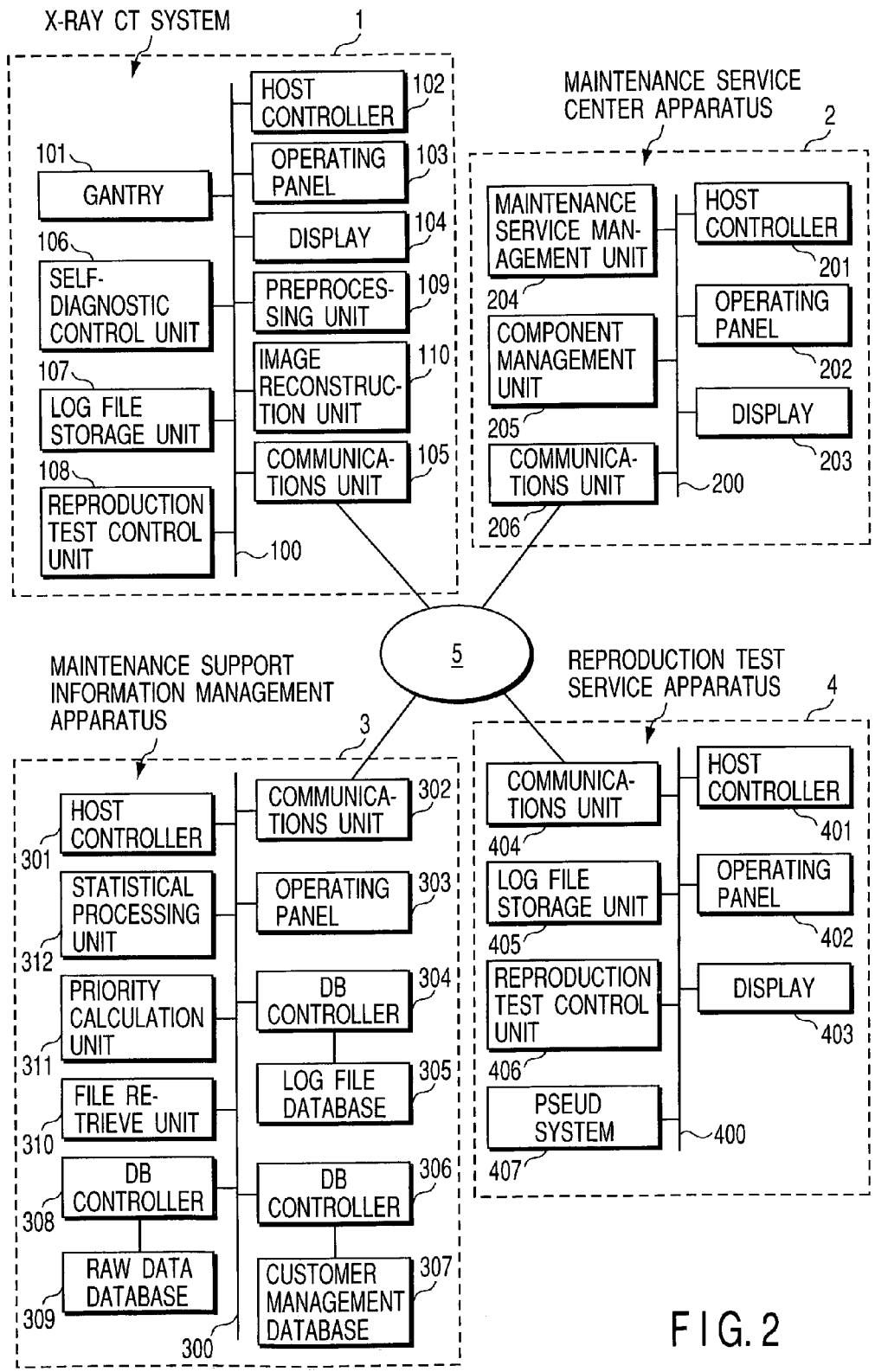
FIG. 2 shows the configuration of the X-ray CT apparatus, maintenance service center apparatus, maintenance support information management apparatus, and reproduction test service apparatus shown in FIG. 1.

FIG. 2 shows the configuration of each of the X-ray CT system 1, the maintenance service center apparatus 2, the maintenance support information management apparatus 3, and the reproduction test service apparatus 4. The X-ray CT system 1 includes a host controller 102, a gantry 101, an operating panel 103, a display 104, and a communications unit 105, which are interconnected by a data/control bus 100.

The gantry 101 includes an X-ray tube, an X-ray detector, a data acquisition system (DAS), a rotation mechanism that holds the X-ray tube and the X-ray detector rotatably, and a driving means for the rotation mechanism. Signals detected by the X-ray detector are amplified and converted into a digital form in the DAS, then subjected to preprocessing, such as sensitivity correction, logarithmic compression, etc., in a preprocessing unit 109 and fed into an image reconstruction unit 110. Data which has been amplified and digitized in the DAS but is not yet preprocessed is referred to as pure raw data. Data which has been preprocessed and is now in the state immediately prior to reconstruction processing is referred to as raw data.

To the data/control bus 100 in the X-ray CT system 1 are further connected a self-diagnosis control unit 106, a log file storage unit 107 and a repeatability test control unit 108. The self-diagnosis control unit 106 activates a self-diagnostic program, developed to detect the presence or absence of a fault and identify the cause of the fault, at regular intervals and at the occurrence of a fault.

The host computer 102 controls the operation of the entire system and generates log files recorded with all operating conditions of the X-ray CT system 1 during the interval from the moment that the power is applied to the system to the moment that the power is turned off. The log files are written with operating conditions on the operating panel 103, communications history, settings of examination plans, fault contents, and so on.

For example, the log file representing the settings of examination plans contains the following items. Usually, the CT system 1 can implement various imaging techniques, such as scanogram imaging, single scan, multi-slice scan, helical scan, real preparation scan(real-prep.scan), CT fluoroscopy, three-section fluoroscopy, etc. In setting up an examination plan, one or more techniques are selected from those imaging techniques and their order is determined. Here, a selected imaging technique is referred to as a subplan. That is, an examination plan is comprised of two or more subplans arranged according to an examination procedure. After subplans have been selected, their imaging conditions, preprocessing conditions, reconstruction conditions and display conditions are set up.

The imaging conditions include the focus position, tube voltage, tube current, tilt angle, scanning time, slice thickness, and FOV (imaging field of view). The preprocessing conditions include various parameters such as an offset correction coefficient, a reference correction coefficient, and a water compensation coefficient. The reconstruction conditions include reconstruction parameters, such as a reconstruction function, filter, the reconstructed slice thickness, the reconstructed slice spacing, a reconstruction matrix, and the reconstructed region center position. The number of subplans that make up an examination plan, the types of the subplans, and the imaging conditions, preprocessing conditions, reconstruction conditions and display conditions of the respective subplans are written into a log file together with patient information.

That is, the each log file is written with all operation-related information. For example, Adjustment values of X-ray CT system imaging conditions X-ray CT system conditions (temperature and voltage of each part, etc.)

X-ray CT system repair record (board replacement, serial number, adjustment, etc.)

X-ray CT system maintenance record (overhaul of each part, etc.)

X-ray CT system inspection record (the results of regular inspections, etc.)

Current version of X-ray CT system software, software version update history, hardware (including furnishings and options) upgrade record, hardware upgrade update history X-ray CT system customizing conditions Images and imaging conditions when the X-ray CT system malfunctions (with images, from a user privacy protection viewpoint, a facility shall be installed which automatically deletes all information and site information that identifies patients)

When the medical system is an MRI apparatus, the log file, for example, contains the following information:

Various adjustment values (RF adjustment value, sequence adjustment value, magnetic field homogenizing adjustment value, etc.)

Conditions (temperature and voltage of each part, liquid helium residual amount, etc.)

Repair record (board replacement, serial number, adjustment, etc.)

Maintenance record (injection of liquid helium, overhaul of each part, etc.)

Inspection record (the results of regular inspections, etc.)

Software/hardware upgrade record (version upgrade record, installation record of furnishings and options, etc.)

Customizing conditions

Images and imaging parameters when the MRI apparatus is malfunctioning (with images, from a user privacy protection viewpoint, a facility shall be installed which automatically deletes all information and site information that identifies patients)

The log file is sent not only to the log file storage unit 107 but also to the maintenance support information management unit 3 over the communications unit 105. The log file storage unit 107, which is subject to limitations in storage capacity, stores two or more log files generated during a recent predetermined period, e.g., the most recent one-month period, on a fast-in fast-out (FIFO) basis. When a fault occurs, pure raw data (or raw data) at that time is stored in the log file storage unit 107 in conjunction with the corresponding log file.

The repeatability test control unit 108 has a function for reading the log file and pure raw data at the occurrence of a fault from the log file storage unit 107 and executing the processes (i.e., pure raw data preprocessing, data transfer, reconstruction, and display) subsequent to data acquisition under the same conditions as those at the occurrence of the fault in accordance with the examination plan recorded in the log file. This processing to reproduce the processes under the same conditions as at the occurrence of a fault and confirm that a recovery has been made after fault correction is referred to as a repeatability test.

The maintenance service center unit 2 is installed in a service central site that provides various services, such as maintenance, correction (repair), etc., to users (X-ray CT systems 1). The unit has a component management unit 205 which manages purchasing, inventory and shipment of components required and a maintenance service management unit 204 which manages the actual work carried out in a maintenance service, including dispatch of service personnel and scheduling of remote maintenance personnel. To the part management unit 205 and the maintenance service management unit 204 are connected a host controller 201, an operating panel 202, a display 203, and a communications unit 206 through a data/control bus 200.

The maintenance support information management unit 3 includes a host controller 301, a communications unit 302, an operating panel 303, a customer management database 307 which stores customer information concerning the CT systems 1 in a group under contract, a controller 306 for the database 307, a log file database 305 which cumulatively stores log files sent from the CT systems 1, a controller 304 for the database 305, a pure raw data database 309 which stores fault-time pure raw data sent from the CT systems 1, a controller 308 for the database 309, a statistical processing unit 312, a priority calculation unit 311, and a file retrieval unit 301, which are interconnected by a data/control bus 200.

The statistical processing unit 312 analyzes log files for each X-ray CT system (user) to calculate statistical indexes, such as the frequency at which faults occur, the frequency of use of every plan, etc. The priority calculation unit 311 calculates the priority of maintenance work based on the statistical indexes and the customer information. These processing units 311 and 312 will be described in detail later.

The reproduction test service unit 4 includes a host controller 401, a communications unit 404, an operating panel 402, a display 403, a storage unit 405 which temporarily stores a log file and pure raw data sent from the maintenance support information management unit 3, a pseudo X-ray CT system (pseudo system) 407 which has facilities to allow for data processing in the range from preprocessing to display but no gantry structure, and a reproduction test control unit 406 which causes the pseudo system 407 to make a reproduction test using the log file and pure raw data stored in the log file storage unit 405, which are interconnected by a data/control bus 400. The reproduction test will be described in detail later.

The operation of the embodiment thus configured will be described next.

Figure 3:
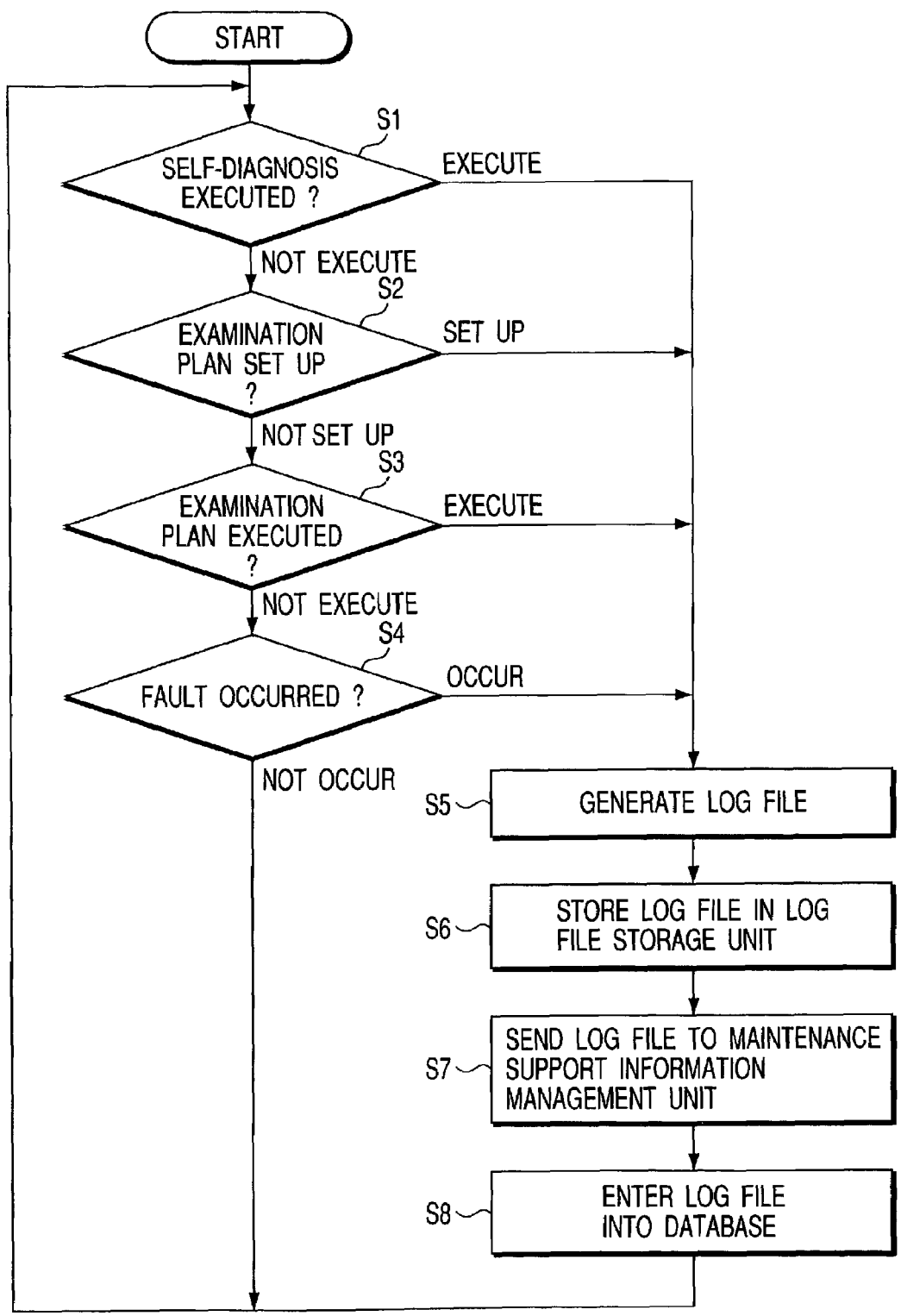
FIG. 3 is a flowchart illustrating the procedure for generating log files saved in the log file database of FIG. 2.

FIG. 3 is a flowchart for the generation and storage of a log file. When a self-diagnostic operation is carried out regularly or at the occurrence of a fault under the control of the self-diagnostic control unit 106 in the X-ray CT system 1 (step S1), a log file that contains the results of the self-diagnostic operation is generated in the host controller 102 (step S5). The generated log file is sent to and stored in the log file storage unit 107 (step S6). The log file storage unit 107 is stored with two or more log files generated during a recent predetermined period, e.g., the most recent one-month period.

The log file that contains the results of the self-diagnosis is sent from the communications unit 105 through the communications circuit 5 to the maintenance support information management unit 3 (step S7) and fed into the log file database 305 (step S8). The storage capacity of the log file database 305 is increased as required. Unlike the log file storage unit 107 in the X-ray CT system 1, therefore, basically the log file database 305 is not subject to limitations in storage capacity. The log file database 305 is therefore stored cumulatively with all log files that have been generated since the installation of each of the X-ray CT systems 1 in a hospital site.

The self-diagnosis is also carried out immediately after the setup of the X-ray CT system 1 in a hospital. Although the self-diagnostic program has been described above as being activated regularly and at the time of a fault, it may be automatically activated when the CT system is idle or at hospital-set particular times in the night.

Specifically, the self-diagnostic operation is carried out as follows. The reconstruction processing unit 110 retains pure raw data (or raw data) for self-diagnosis. The self-diagnostic pure raw data contains data for self-diagnosis of data transfers between gantry and console (data transfer management board: DTB), between DTB (Data Transfer management Board) and preprocessing unit 109, between preprocessing unit and disk drive, between disk drive and DTB, between disk drive and reconstruction board, between reconstruction boards, between reconstruction board and DTB, between processing boards, between DTB and system management board, between reconstruction board and system management board, and between system management board and host controller, data processing, data management, memory access, and disk access. Based on the self-diagnostic data, checks are made as to whether processing is completed within a standard time, whether the reconstructed image data is displaced from the reference image data, etc., to thereby detect normal operation, operational instability, the possibility of occurrence of a fault, or the occurrence of a fault. The results of the self-diagnosis are sent to the units 2 and 3 as a log file.

In locating a fault, the self-diagnostic program analyzes which hardware (boards and components) is faulty based on check points and the contents of the fault and sends the results to the units 2 and 3 in the form of a log file. This self-diagnostic history helps to initially determine whether the cause of the fault lies in hardware or software.

Prior to the shipment of products, hardware and firmware testing programs are run for self-diagnosis under the reconstruction condition in which a load is imposed on the reconstruction unit 110 to decide the acceptance or rejection of the products. At the time of activation of the CT system 1 (power-on time), checks are made on the boards, main components, transmission unit, etc., built into the reconstruction processing unit 110; that is, hardware-related self-diagnosis is carried out, on the whole. The preprocessing unit 109 always monitors a portion of pure raw data to be preprocessed to confirm instantly that no data shift has occurred. At the time of reconstruction processing, even in the middle of reconstruction, diagnostic programs for data, processing and transmission management always monitor and record where in each of the reconstruction boards faults occur, helping identify the cause of the fault.

Measures against faults after shipment will be to provide service personnel with hardware and firmware testing programs and to investigate the cause of faults. These programs are run to subject a board or system in which a fault has been located to a load test under the reconstruction conditions in which a load is imposed on the reconstruction processing unit 110, thereby identifying the cause of the fault.

Returning to FIG. 3, when the examination plan is set up (step S2), a log file containing the contents of the examination plan is generated in the host controller 103 in the X-ray CT system 1 (step S5). This log file is sent to and stored in the log file storage unit 107 (step S6) and, at the same time, transmitted from the communications unit 105 through the communications circuit 5 to the maintenance support information management unit 3 (step S7) and then stored in the log file database 305 (step S8).

In the X-ray CT system 1, when the examination plan is executed (step S3), the host controller 102 generates a log file that contains a record of the examination plan execution (step S5). This log file is sent to the log file storage unit 107 (step S6) and, at the same time, transmitted from the communications unit 105 through the communications circuit 5 to the maintenance support information management unit 3 (step S7) and then stored in the log file database 305 (step S8).

In the X-ray CT system 1, when a fault occurs (step S4), the host controller 102 generates a log file that contains a record of operation at the occurrence of the fault (step S5). Together with pure raw data at that time, this log file is sent to the log file storage unit 107 (step S6) and, at the same time, transmitted from the communications unit 105 through the communications circuit 5 to the maintenance support information management unit 3 (step S7) and then stored in the log file database 305 (step S8).

Figure 4:
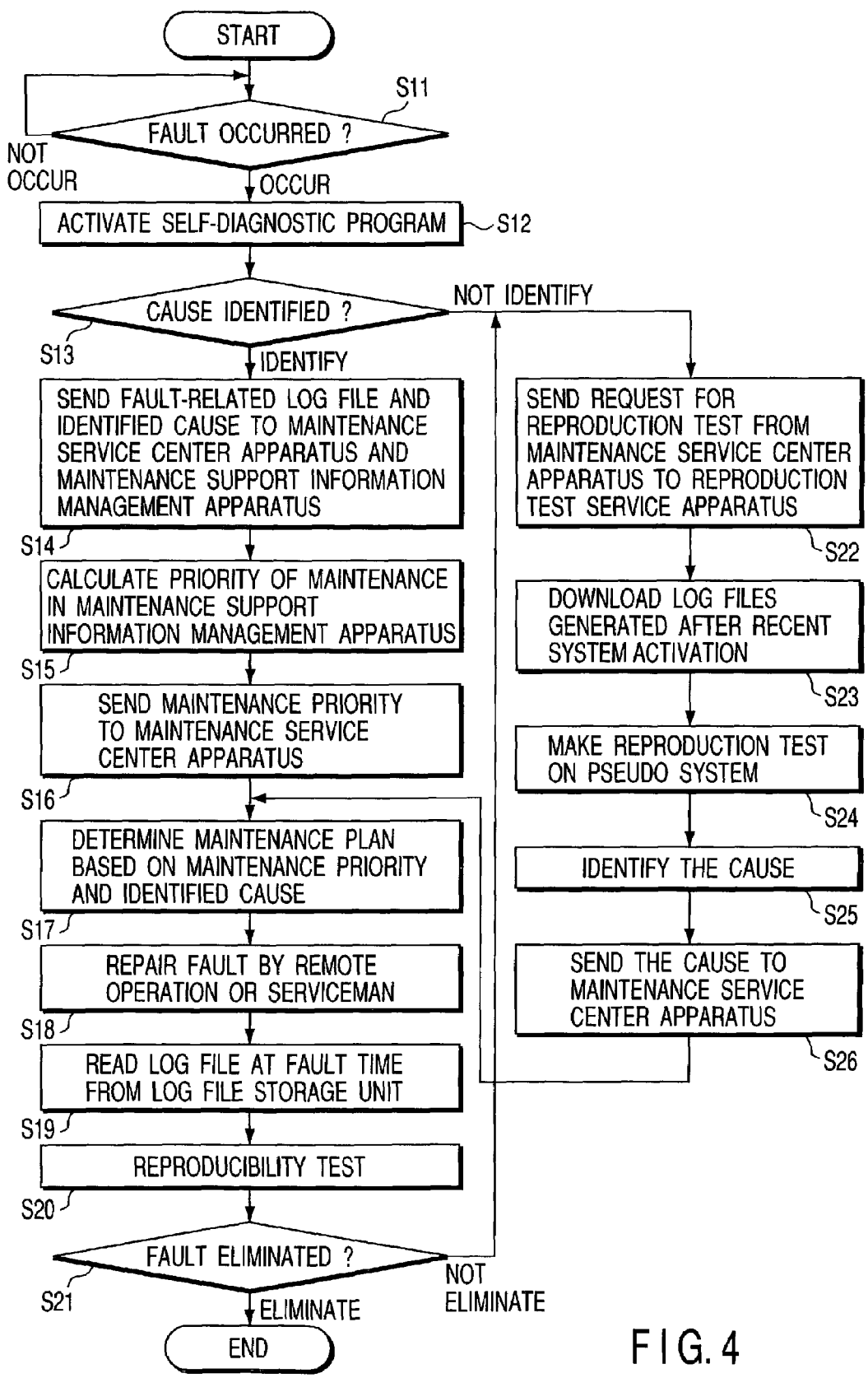
FIG. 4 is a flowchart illustrating the operating procedure in the event of a fault.

The operation at the occurrence of a fault will be described next with reference to FIG. 4. When a fault occurs in one of the X-ray CT systems 1 (step S11), the self-diagnostic program is activated under the control of the self-diagnostic unit 106 in that X-ray CT system to carry out the self-diagnostic operation (step S12).

The self-diagnostic program, in addition to the facility to identify the cause of a fault, has a facility to decide whether the cause results in system going down or is such that no fault occurs in other operations than a specific operation. In accordance with the result of this decision, a message to the CT system operator is displayed on the screen of the display 104, which describes that the entire system is unavailable or only the specific operation is unavailable (degenerate operation). Examples of messages are such that "reconstruction processing will be delayed", "CT fluoroscopy mode (an image is reconstructed without delay relative to scan) is unavailable", "occurrence of a fault that makes diagnosis difficult", etc. For example, the current fault may be displayed by an icon in an area of the screen which is not obstructive to image display. Alternatively, the form of display of an icon for the soft switch of the reconstruction mode or the reconstruction module in which a fault has occurred may be changed to opacity, gray, or a specific color. Further, for remote maintenance, a warning icon or mark may be displayed.

When the cause of the fault is identified by the self-diagnostic operation (step S13), the log file at the occurrence of the fault and the identified cause are transmitted to the maintenance service unit 2 and the maintenance support information management unit 3 together with a request for repair (step S14).

The maintenance support information management unit 3 calculates the priority of maintenance for that fault (step S15).

Figure 5:
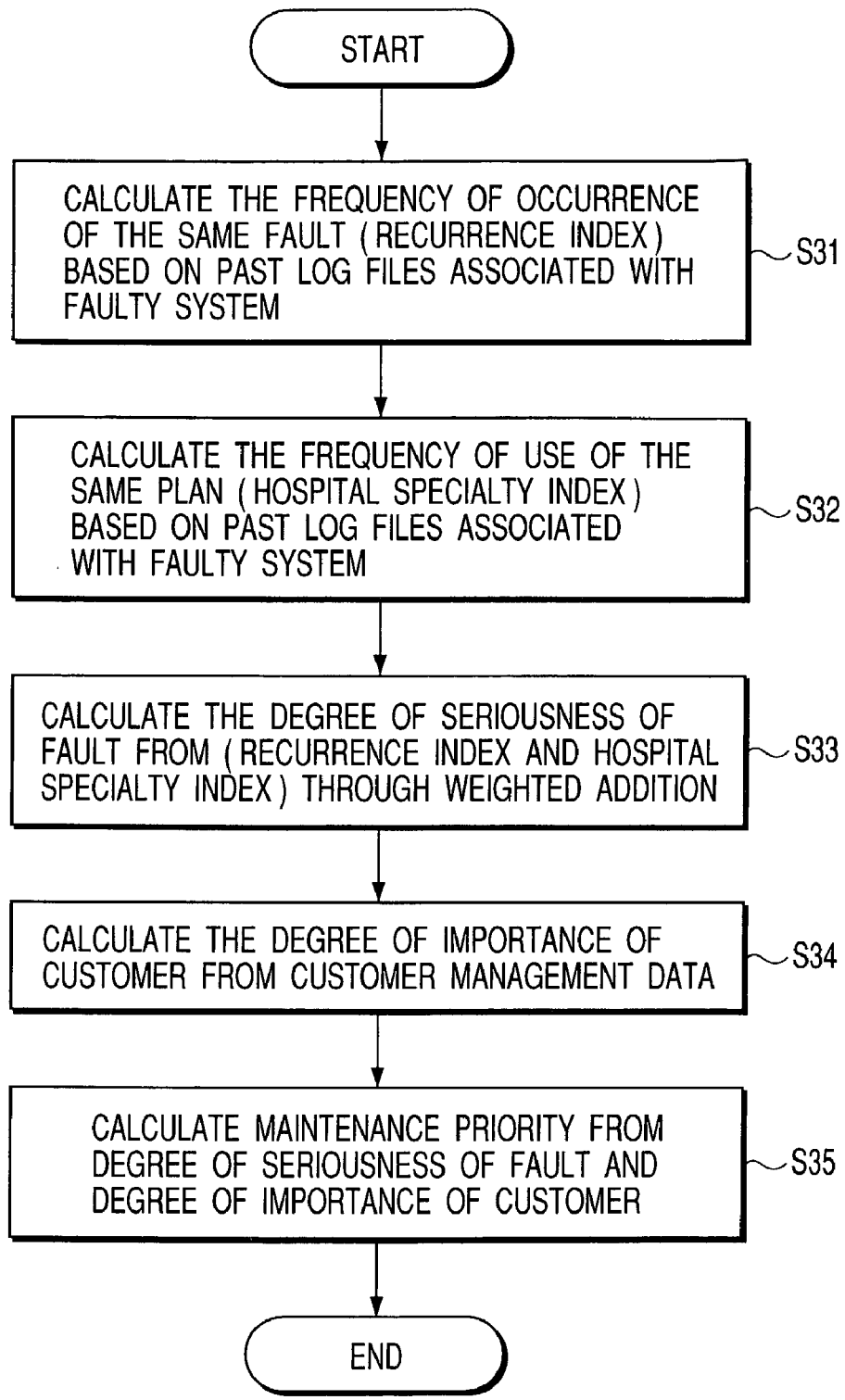
FIG. 5 is a flowchart illustrating the procedure for determining the maintenance priority in FIG. 4.

In FIG. 5, there is shown the procedure of calculating the priority of maintenance. First, all the past log files associated with the faulty X-ray CT system are retrieved from the log file database 305 by the file retrieval unit 310 and then read into the statistical processing unit 312. The statistical processing unit analyzes these past log files to calculate the past frequency of occurrence of the same fault (step S31). The frequency of occurrence represents the repeatability of occurrence of the same fault in the faulty X-ray CT system. The frequency of occurrence is normalized to obtain the repeatability index.

The statistical processing unit 312 analyzes all the past log files of the faulty CT system to calculate the frequency of use of an examination plan identical or similar to the examination plan in which the fault occurred (step S32). When the frequency of use of this examination plan is relatively high, it is considered that the hospital is relatively high in specialty to that examination, that is, that the unavailability of that examination plan has a relatively high degree of influence on examination work. Conversely, when the frequency of use of that examination plan is relatively low, it is considered that the hospital is relatively low in specialty of that examination, that is, that the unavailability of that examination plan has a relatively low degree of influence on examination work. The frequency of use is normalized to obtain the specialty index.

A self-learning facility may be introduced into the statistical processing. An example of self-learning is to record the number of times reconstruction modes are allocated to expert plans. As to batch reconstruction as well, reconstruction modes used should also be recorded. Each time reconstruction is carried out, the number of times the reconstruction mode is carried out is recorded and updated. Self-learning is set to take place in units of weeks, months, or years. "Batch reconstruction" refers to reconstructing pure raw data or raw data already collected under the same reconstruction conditions as at the time of scan or under the modified reconstruction conditions.

The recurrence index and the specialty index are multiplied by their respective corresponding weighting coefficients and then added together in the statistical processing unit 312 to calculate a degree of seriousness of the fault (step S33). Although the weighting coefficient for the recurrence index and the weighting coefficient for the specialty index are typically identical to each other, they may be set to different values. The statistical processing unit can revise the degree of seriousness of the fault based on the system individual situation, such as the time that has elapsed after replacement of reconstruction processing software, the version of software in use, the software version update history, whether or not the faulty component is a main component, etc. Whether to decide the degree of seriousness of the fault is decided by the operator.

Next, the statistical processing unit 312 calculates the degree of importance of the customer based on customer information stored in the customer management database 307 (step S34). Customer information used to calculate the degree of importance of the customer includes its individual situations, such as whether the hospital has a strong social influence on the sale of the system, whether the hospital is one which has switched from one company's system to another company's system, the sentiment of the customer, the system scale, the results of supply of the CT system and other systems to the entire hospital, etc. Actually, the database manager receives the individual customer situation from the sales division at system supply time or when necessary, then digitizes, registers and updates them. The most recent values of these pieces of information are weighted and then added together in the statistical processing unit 312.

Finally, in the priority calculation unit 311, the maintenance priority is calculated based on the degree of seriousness of the fault and the degree of importance of the customer. For example, the degree of seriousness of the fault and the degree of importance of the customer are added simply or weighted and added to obtain the maintenance priority.

Returning now to FIG. 4, the maintenance priority thus calculated is sent from the communications unit 302 of the maintenance support information management unit 3 over the communications circuit 5 to the maintenance service center unit 2 (step S16). In the maintenance service center unit 2, by reference to the maintenance priority and the cause of the fault identified through self-diagnosis, the maintenance manager makes a maintenance plan containing repair times and repair contents with confirmation of components in stock and the present state of the maintenance system such as schedules of service personnel (step S17).

According to the maintenance plan determined, repair work is carried out through remote operation or service personnel at the system site (step S18). To determine whether the X-ray CT system has recovered from the fault, after the repair work the log file and pure raw data at the occurrence of the fault are read from the log file storage unit 107 to the repeatability test control unit 108 (step S19) and a repeatability test is made under the same conditions as at the occurrence of the fault (step S20).

Here, the difference between a repeatability test and reproduction test will be explained. The reproduction test, which will be described in detail later, is a test which is carried out rigorously in the system maker site for the purpose of identifying the cause of faults. On the other hand, the repeatability test is a test which is carried out in the hospital site for fault recovery confirmation and, as described above, does no more than determine whether or not a fault will recur under the same conditions as at the occurrence of that fault.

If the repeatability test shows that the fault has been corrected (step S21), then the repair work is complete. Otherwise, it is possible that the cause of the fault identified through the self-diagnostic program is in error. This situation should be handled identically to the case where the cause of the fault cannot be identified through the self-diagnostic program.

When the cause of the fault cannot be identified through the self-diagnostic program (step S13), a request for reproduction test is sent from the maintenance service center unit 2 to the reproduction test service unit 4 (step S22). The same applies to the case where the repeatability test shows that the fault has not been corrected.

Here, an outline of the reproduction test is given first. The fault correction needs a reproduction test. Upon receipt of the previously described log file, the pseudo system 407 automatically reads the reconstruction conditions at the occurrence of the fault from the log file storage unit 405 and enters a pseudo operation. In the event of a fault whose cause cannot be identified by service personnel at the site of that fault, the fault identification needs information as to what the reconstruction conditions were like, the presence or absence of raw data for reproduction test, the contents of processing immediately prior to the occurrence of the fault, etc. Reproduction tests include one using the pseudo system 407, one using the reproduction processing unit, and one using the pseudo system 407 (which has neither gantry nor bed but is configured to operate as if the gantry were present). The most straightforward system is to allow phenomena which occurred at the site of the fault to be reproduced by simply loading a log file recorded with the situations at the occurrence of the fault (reconstruction conditions, system parameters, etc.) into the repeatability test control unit 108 in the CT system. The ability to conduct reproduction tests is absolutely necessary in finding faults. If reproduction cannot be performed, finding the fault may require considerable time and effort. As long as that log file is present, the implementation of a device for reproduction allows the time required to identify the cause to be reduced significantly, and human error to be eliminated.

To allow the reproduction unit in the pseudo system 407 to reproduce the fault, pure raw data (or raw data) is required in addition to the above log file. The reconstruction processing unit, which is not a complete product, is often different from products in installed system management software and is thus not suitable for processing of faults involved in such software. The presence of the fault-related log file allows identical system parameters to be used and consequently fault reproduction to be made anywhere with ease. The pseudo system 407 is a CT system which has system management software as well as a reproduction processing unit installed and operates as if it were equipped with a gantry and thus makes the identification of the cause of the fault easier. Without the provision of a complete CT system having a gantry and a bed, which take up a lot of space, a pseudo CT system which functions identically to a product CT system similar to the complete CT system allows the cause of the fault to be identified.

For reproduction, a list of test items (scans, reproductions) is displayed on the system. The reproduction test engineer is allowed to select whether to perform all the items or whether to perform only processing of the most recent scan, reproduction, etc. The log file output from the CT system is written with reconstruction conditions and so on, which can be used to identify the cause of the fault occurring according to the order of processing. In most cases, a fault occurs in association with a processing, but not independently. It thus becomes possible to load the associated log file into the pseudo system 407 and make a fault test while following the history. The employment of system parameters, reconstruction conditions, scan conditions, pure raw data, and raw data which were preserved at the occurrence of a fault allows confirmation to be made as to whether the fault is reproduced. In the event that the fault is not reproduced, the reproduction test is continued while sequentially following the past histories, beginning with the most recent one, to read the past reconstruction conditions.

That is, at the time of a fault test, the pseudo system 407 and its associated control unit 406 automatically traces the fault. The reproduction tests are made while tracing the previously described histories back one after another. The hardware and software diagnostic programs continue to monitor faults. When the fault is reproduced, the engineer in charge of the test is informed of it through radio, sound, light, flashing screen, etc. (by sending mail or calling him via cellular phone). The pseudo system 407 stops in a state where the log file at that time is output. At the time of a fault test, therefore, the person in charge need not remain at the pseudo system site.

During the reproduction test, the pseudo system 407 is temporarily stopped in the event that the load on an individual unit becomes maximum. During the reproduction test, surrounding people are notified through display or sound that a reproduction test is being made. Also, all the engineers in charge involved in the pseudo system are notified via radio, cable, mail, or the like of the state the pseudo system is placed in. To prevent the pseudo system from being used imprudently, a lamp is turned on to notify that a reproduction test is initiated. Means may be provided by which, when a person is approaching the pseudo system in operation, he or she is notified.

After the termination of the reproduction test, even if the engineer in charge forgets to store the reproduction test data, the pseudo system automatically stores the reproduction test log file, reproduced data, scan conditions and images in a specified location and notifies that the reproduction test is complete. Thus, upon reproduction testing, the engineer in charge need not remain at the pseudo system site. After the completion of reproduction, the pseudo system automatically resumes the initial state.

Return is made to FIG. 4. Upon receiving a reproduction test request, the host controller 401 of the reproduction test service unit 4 requests the maintenance support information management unit 3 to download all log files associated with the faulty X-ray CT system generated after its recent system activation time and pure raw data at the time of the fault (step S23). The recent system activation time is, for example, the time when the system power was turned on in the morning on the day of the fault or, if the faulty X-ray CT system is a 24-hour operating system, the last time the system power was switched on. In the latter case, this may go back several days or several weeks. Those log files and pure raw data are temporarily stored in the log file storage unit 405.

Using the downloaded log files and pure raw data, the reproduction test control unit 406 implements a reproduction test in the pseudo X-ray CT system (pseudo system) 407 which has a range of data processing facilities from preprocessing to display but no gantry structure. The reproduction test greatly differs from the repeatability test in that the repeatability test does no more than reproduce the operating state at the time a fault occurred. On the other hand, the reproduction test first reproduces the subplan at the time the fault occurred and then reproduces each of the previously executed subplans in sequence in reverse order of execution until the cause of the fault is identified. Return may be made, at best, to the operation state of the system at the time of last switch-on.

Such a reproduction test allows identification of faults that cannot occur upon execution of individual subplans, that is, faults that occur when subplans and/or plans are combined, that is, a very rare but very serious fault which may occur due to bugs or errors in the very basic operations that form the basis of the system, such as data transfer control, working memory control, etc. A case has been reported in which such a fault is caused by data transmission errors or data erase errors in the working memory under peculiar circumstances that the same or different subplans are executed one after another.

When the cause of the fault is identified through such a retracing reproduction test (step S25), it is sent to the maintenance service center unit 2 together with information concerning measures organized on the maker side (e.g., firmware updates) (step S26).

The maintenance service center unit 2 forms a maintenance plan in accordance with the cause of the fault and the measures (step S17) and then repairs the fault (step S18).

Figure 6:
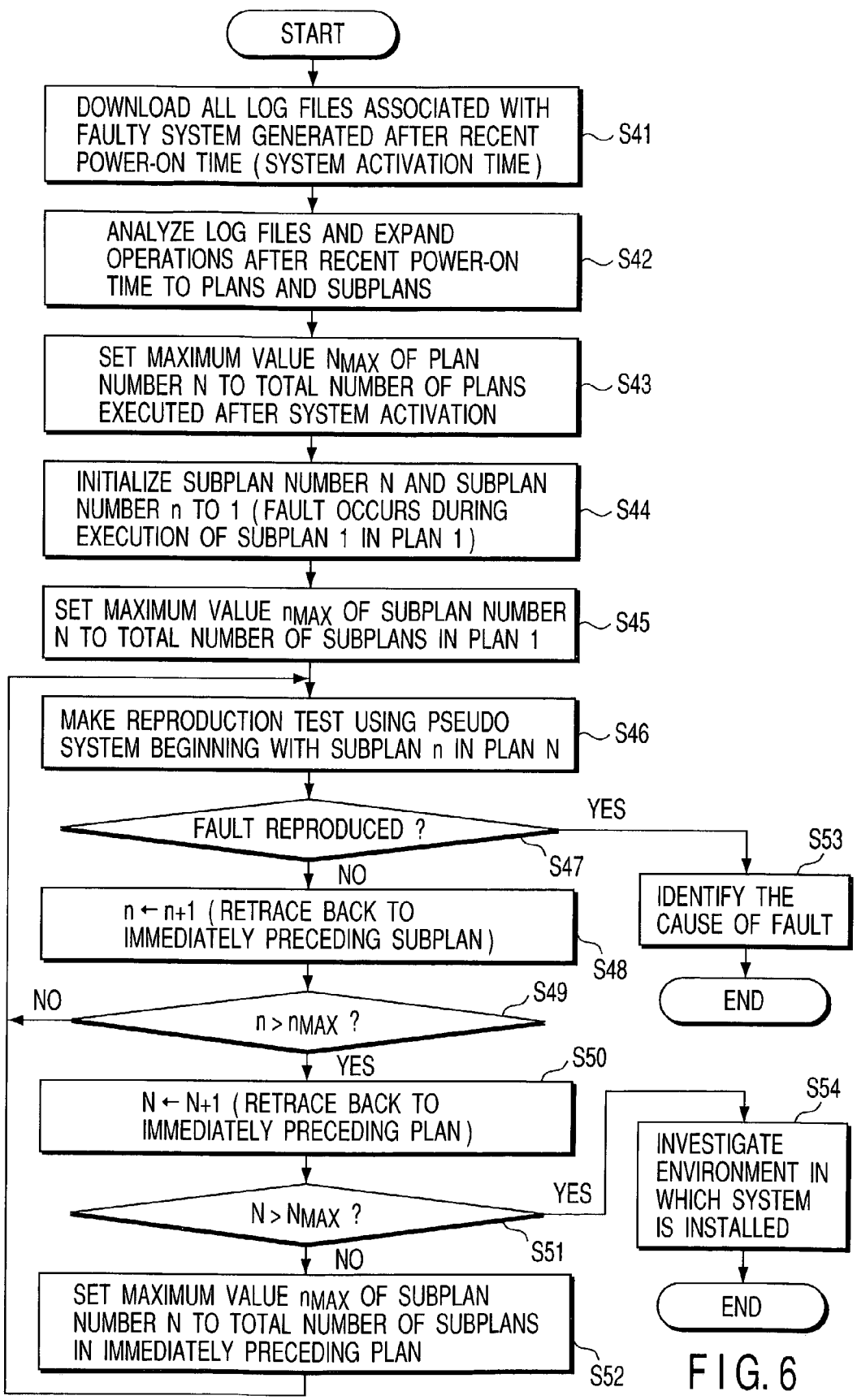
FIG. 6 is a flowchart illustrating the reproduction test procedure in FIG. 4.
Figure 7:
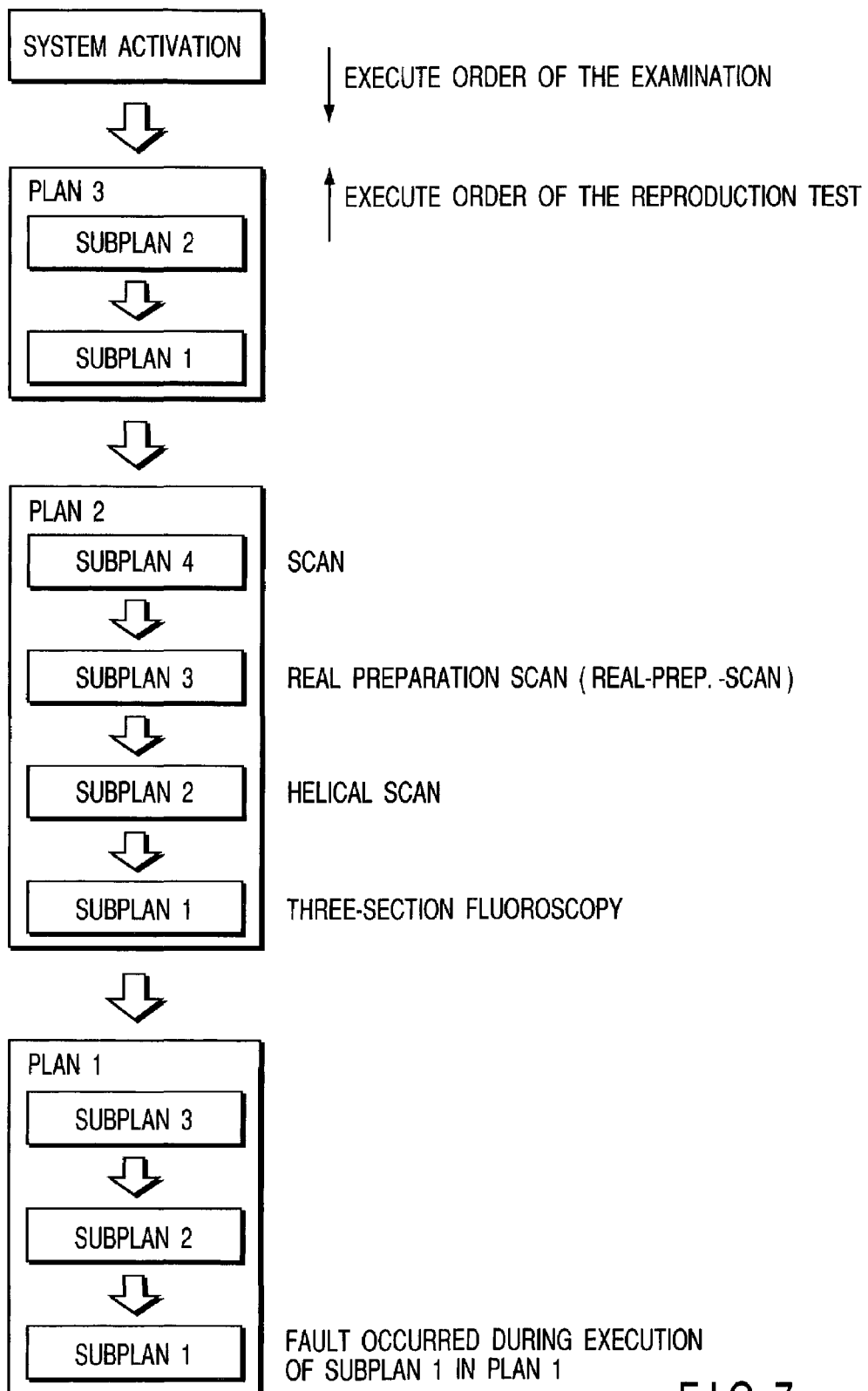
FIG. 7 is a supplementary diagram for the reproduction test procedure in FIG. 6 and illustrates an example of a plan execution sequence from the time of system startup.

Next, the reproduction test made by the reproduction test service unit at the maker site will be described in detail. FIG. 6 shows the reproduction test procedure. FIG. 7 shows exemplary examination plans and subplans carried out in the X-ray CT system 1 during the time interval from the system activation to the time when a fault has occurred. Here, two variables N and n are introduced for convenience of description. N represents the plan number to provide plan identification and n represents the subplan number for subplan identification. It should be noted that the newer the plans and subplans are, the lower the number assigned to them is. That is, in the example of FIG. 7, an examination plan numbered 3 is carried out first after system activation. The examination plan numbered 3 includes two subplans: subplan 2 and subplan 1. The subplan 2 is carried out first and the subplan 1 is carried out next. Subsequent to the examination plan 3, the examination plan 2 is executed, which contains four subplans. Each of these subplans is executed in sequence beginning with the subplan 4. Subsequent to the examination plan 2, the examination plan 1 is executed, which contains three subplans. Each of these subplans is executed in sequence beginning with the subplan 3. It is assumed here that a fault has occurred while the subplan 1 in the examination plan 1 is in execution.

As shown in FIG. 6, all log files associated with the faulty X-ray CT system 1 since its recent system activation time and pure raw data at the time of the fault are downloaded from the maintenance support information management unit 2 into the log file storage unit 405 where they are stored temporarily (step S41). The reproduction test control unit 406 analyzes the downloaded log files to extract all plans and subplans executed during the interval from the time of the recent system activation to the time of the fault (step S42).

The total number of plans executed after the system has been activated is set as the maximum number $N_{MAX}$ of N (step S43). In the example of FIG. 7, $N_{MAX}=3$. N is initialized to 1 and n is initialized to 1 (step S44). It is assumed here that the fault occurred during the execution of the subplan 1 in the plan 1. The total number of subplans in the plan 1 is set as the maximum number $n_{MAX}$ of n.

After the above initial preparations have been made, the reproduction test is actually initiated. First, pure raw data collected through the subplan 1 in the plan 1 at the time of the fault is fed into the pseudo system 407 where it is subjected in turn to preprocessing, reconstruction, and display under the same conditions (data transfer conditions, reconstruction conditions, display conditions, etc.) as in the subplan 1 (step S46).

If the fault is not reproduced through the first reproduction test (step S47), then n is incremented by one to 2 (step S48). If the maximum value, nMAX, (3 in this example) is not exceeded (step S49), then the reproduction test is carried out with the immediately preceding subplan 2 (step S46). That is, the same operation as in the subplan 2 carried out one subplan prior to the subplan at the time of the fault is reproduced, and then the same operation as in the subplan 1 at the time of the fault is reproduced.

If even the reproduction test with the subplan of one subplan before fails to reproduce the fault, then the procedure goes through steps S48 and S49 to step S46 to make the reproduction test with the subplan 3 of still another subplan before (step S46). That is, the same operation as in the subplan 3, the same operation as in the subplan 3 and the same operation as in the subplan 1 are carried out in succession on the pseudo system 407.

If, even at this stage, the fault is not reproduced (step 47), the procedure goes through steps S48 and S49 to step S50 in which the plan number N is incremented by one. This means that the reproduction test goes back to the plan one plan prior to the plan in which the fault occurred.

If the plan number N (here 2) incremented by one is less than the total number of plans from the time of system activation (the maximum number NMAX (here 3) of the plan number) (step S51), the procedure goes to step S52, so that the total number of subplans in the plan 2 of one plan before is set as the maximum number nMAX of the subplan number.

Return is made to step S46 to resume the reproduction test from the most recent subplan 1 in the plan 2.

Thus, until the fault is reproduced, the reproduction test is executed while retracing back to each of the subplans in sequence. Depending on circumstances, the reproduction test is made while retracing back to each of the plans in sequence. When the fault is reproduced at some stage (YES in step S47), the procedure goes to step S53 to identify the cause of the fault based on conditions of the fault.

If the fault is not reproduced (YES in step S51) irrespective of the reproduction test on the subplan (subplan 2) in the plan (plan 3) first executed after system activation, there is little possibility that the cause is inherent in the X-ray CT system. In that case, it is supposed that the cause of the fault lies in the environment in which the faulty X-ray CT system is installed and hence the procedure goes to step S54 to investigate the environment.

Thus, by making the reproduction test while going back to each of the subplans in sequence, and depending on circumstances, while going back to each of the plans in sequence until the fault is reproduced, it becomes possible to identify a fault which will not occur by execution of individual subplans, that is, a fault which will not occur until subplans and/or plans are combined, that is, a very rare but very serious fault which will occur due to bugs or errors in the very basic operations that form the basis of the system, such as data transfer control, working memory control, etc.

According to the present invention, as described above, the cause of a fault in medical systems can be identified in a short time, allowing the fault to be corrected quickly and the system downtime to be reduced. The present embodiment effectively works not only under circumstances that the medical system goes down but also on such a fault as to only make some functions or modes unavailable without causing the system to go down.

Additional advantages and modifications will readily occur to those skilled in the art. Therefore, the invention in its broader aspect is not limited to the specific details and representative embodiments shown and described herein. Accordingly, various modifications may be made without departing from the spirit or scope of the general inventive concept as defined by the appended claims and their equivalents.

What is claimed is:

1. A reproduction test service apparatus configured to reproduce past operations of a medical system, comprising:
a unit configured to receive a plurality of log files directly or indirectly from the medical system through a communication circuit, the log files indicating the past operations of the medical system;
a unit configured to store the plurality of log files;
a pseudo medical system; and
a control unit configured to control the pseudo medical system, based on the log files, so as to reproduce the past operations of the medical system on the pseudo medical system,
wherein the unit configured to receive the log files is further configured to receive at least one of pure raw data and raw data, the pure raw data being data converted from signals detected by the medical system, the raw data being data processed from the pure raw data, and
the control unit is further configured to control the pseudo medical system based on the at least one of the pure raw data and the raw data.

2. The apparatus according to claim 1, wherein the pseudo medical system reproduces the past operations of the medical system while retracing back through the past operations one after another according to an operation history of the medical system.

3. The apparatus according to claim 2, wherein the pseudo medical system automatically stops the reproducing operation when the same conditions, as when the fault occurred in the medical system, are reproduced by the pseudo medical system.

4. The apparatus according to claim 1, wherein the pseudo medical system differs from the medical system at least in that the pseudo medical system has neither a gantry nor a bed.

5. The apparatus according to claim 1, wherein the unit configured to receive a plurality of past log files receives pure raw data or raw data together with the log files.

6. The apparatus according to claim 1, wherein the pseudo medical system reproduces the past operations under the same reconstruction conditions as with the past operations of the medical system.

7. The apparatus according to claim 1, wherein the pseudo medical system reproduces the past operations under the same system operating conditions as with the past operations of the medical system.

8. The apparatus according to claim 1, further comprising an operating unit configured to set up conditions of the past operations to be reproduced by the pseudo medical system.

9. The apparatus according to claim 1, wherein the plurality of log files are ones which have been generated since the medical system was last activated.

10. The apparatus according to claim 1, further comprising an indication unit configured to indicate the pseudo medical system is in reproducing operation.

11. The apparatus according to claim 1, wherein the along files are base on data generated by the medical system.

* * * * *